US011122802B2

(12) United States Patent
Puente De Vera et al.

(10) Patent No.: US 11,122,802 B2
(45) Date of Patent: Sep. 21, 2021

(54) SOIL TREATMENT

(71) Applicant: EVONIK OPERATIONS GMBH, Essen (DE)

(72) Inventors: Fernando Puente De Vera, Saragossa (ES); Jose M. Lopez Martinez, Barcelona (ES); John M. Rovison, Sanborn, NY (US); Weidong An, Williamsville, NY (US)

(73) Assignee: Evonk Operations GmbH, Essen (DE)

( * ) Notice: Subject to any disclaimer, the term of this patent is extended or adjusted under 35 U.S.C. 154(b) by 0 days.

(21) Appl. No.: 16/936,663

(22) Filed: Jul. 23, 2020

(65) Prior Publication Data
US 2020/0352165 A1    Nov. 12, 2020

Related U.S. Application Data

(63) Continuation of application No. 15/785,544, filed on Oct. 17, 2017, now abandoned.

(60) Provisional application No. 62/409,525, filed on Oct. 18, 2016.

(51) Int. Cl.
    *A01N 37/16*      (2006.01)
    *A01M 17/00*      (2006.01)

(52) U.S. Cl.
    CPC ........... *A01N 37/16* (2013.01); *A01M 17/002* (2013.01)

(58) Field of Classification Search
    CPC ........ A01N 59/00; A01N 37/16; A01N 25/30; A01M 17/002; A61L 2/0088; A61L 2/186
    See application file for complete search history.

(56) References Cited

U.S. PATENT DOCUMENTS

| | | | |
|---|---|---|---|
| 5,122,538 A | 6/1992 | Lokkesmoe et al. | |
| 5,168,655 A | 12/1992 | Davidson et al. | |
| 5,439,663 A | 8/1995 | Manganaro et al. | |
| 5,518,692 A | 5/1996 | Grech et al. | |
| 5,607,856 A * | 3/1997 | Moon | A01N 37/16 422/28 |
| 5,632,676 A | 5/1997 | Kurschner et al. | |
| 5,849,985 A | 12/1998 | Tieckelmann et al. | |
| 5,879,653 A | 3/1999 | Castrantas et al. | |
| 5,977,403 A | 11/1999 | Byers | |
| 6,028,104 A | 2/2000 | Schmidt et al. | |
| 6,168,808 B1 * | 1/2001 | Hamon Godin | A01N 37/16 424/126 |
| 6,365,099 B1 | 4/2002 | Castrantas et al. | |
| 6,828,294 B2 | 12/2004 | Kellar et al. | |
| 7,347,647 B2 | 3/2008 | Seech et al. | |
| 7,416,718 B2 | 8/2008 | Sethi et al. | |
| 7,473,372 B2 | 1/2009 | Block et al. | |
| 7,510,721 B2 | 3/2009 | Roden et al. | |
| 7,524,141 B2 | 4/2009 | Sethi et al. | |
| 7,547,430 B2 | 6/2009 | Sethi et al. | |
| 7,576,254 B2 | 8/2009 | Block et al. | |
| 7,666,315 B2 | 2/2010 | Lopez Martinez et al. | |
| 7,785,038 B2 | 8/2010 | Block et al. | |
| 7,947,745 B1 | 5/2011 | Laramay et al. | |
| 7,998,446 B2 | 8/2011 | Pfeffer et al. | |
| 8,029,693 B2 | 10/2011 | Dada et al. | |
| 8,454,890 B2 | 6/2013 | Rovison, Jr. et al. | |
| 8,486,366 B2 | 7/2013 | Pfeffer et al. | |
| 8,575,075 B2 | 11/2013 | Huang et al. | |
| 8,877,149 B2 | 11/2014 | Pfeffer et al. | |
| 9,005,669 B2 | 4/2015 | Allen et al. | |
| 9,018,142 B2 | 4/2015 | Rovison, Jr. et al. | |
| 9,114,357 B2 | 8/2015 | Block et al. | |
| 9,295,744 B2 | 3/2016 | Rovison et al. | |
| 9,321,664 B2 | 4/2016 | Li et al. | |
| 9,351,488 B2 | 5/2016 | Rovison et al. | |
| 9,375,768 B2 | 6/2016 | Pisanova et al. | |
| 9,656,890 B2 | 5/2017 | Block | |
| 9,821,353 B2 | 11/2017 | Pisanova et al. | |
| 9,849,203 B2 | 12/2017 | Rovison, Jr. et al. | |
| 10,344,199 B2 | 7/2019 | Pisanova et al. | |
| 10,568,322 B2 | 2/2020 | Man et al. | |
| 10,625,655 B2 | 4/2020 | Rovison, Jr. et al. | |
| 2003/0129254 A1 | 7/2003 | Yasuhara et al. | |
| 2005/0152991 A1 | 5/2005 | Man et al. | |
| 2007/0010420 A1 | 1/2007 | Lange et al. | |
| 2007/0264369 A1 * | 11/2007 | Moon | A01N 65/08 424/771 |

(Continued)

FOREIGN PATENT DOCUMENTS

| | | |
|---|---|---|
| CN | 103843817 | 6/2014 |
| EP | 0035800 | 9/1981 |

(Continued)

OTHER PUBLICATIONS

Kao (AKYPO LF2 Product Specification) (Year: 2020).*
International Search Report for corresponding international application, PCT/US2017/056857 filed Oct. 17, 2017.
Written Opinion of the International Searching Authority for corresponding international application, PCT/US2017/056857 filed Oct. 17, 2017.
International Preliminary Report on Patentability for corresponding international application, PCT/US2017/056857 filed Oct. 17, 2017.
Extended European Search Report dated Mar. 11, 2020 in corresponding European application EP 17861784.1.
International Search Report for international application PCT/US2019/037957, filed Jun. 19, 2019; (corresponds to copending U.S. Appl. No. 17/253,953).

(Continued)

*Primary Examiner* — Robert A Wax
*Assistant Examiner* — Quanglong N Truong
(74) *Attorney, Agent, or Firm* — Law Office of: Michael A. Sanzo, LLC

(57) ABSTRACT

The present invention relates to compositions and formulations for soil disinfection against a wide spectrum of plant pathogens and pests. More particularly, the formulation comprising (i) peracids, such as peracetic acid and an GO anionic surfactant, such as capryleth-9 carboxylic acid is synergistically effective in treatment of soil to control plant parasitic nematodes and soil-borne plant pathogens such as bacteria, spores and fungi.

19 Claims, No Drawings

(56) References Cited

U.S. PATENT DOCUMENTS

| | | |
|---|---|---|
| 2008/0226541 A1 | 9/2008 | Zhou et al. |
| 2010/0240765 A1 | 9/2010 | Lange et al. |
| 2010/0279906 A1 | 11/2010 | Schwarz et al. |
| 2011/0311645 A1 | 12/2011 | Diaz |
| 2013/0203849 A1* | 8/2013 | Ben Yehuda .......... A01N 25/22 514/557 |
| 2013/0344556 A1 | 12/2013 | Fernholz et al. |
| 2014/0194335 A1 | 7/2014 | Gu et al. |
| 2014/0228328 A1 | 8/2014 | Rovison et al. |
| 2015/0005379 A1 | 1/2015 | Block et al. |
| 2015/0141301 A1 | 5/2015 | Rovison, Jr. et al. |
| 2015/0218437 A1 | 8/2015 | Rovison, Jr. et al. |
| 2015/0239738 A1 | 8/2015 | Zhou et al. |
| 2015/0258589 A1 | 9/2015 | Seech |
| 2016/0176735 A1 | 6/2016 | Balasubramanian et al. |
| 2016/0150779 A1 | 7/2016 | Li et al. |
| 2016/0345576 A1 | 12/2016 | Rovison et al. |
| 2017/0248522 A1 | 8/2017 | Li et al. |
| 2017/0313604 A1 | 11/2017 | Garibi et al. |
| 2018/0042249 A1 | 2/2018 | Bullard et al. |
| 2018/0065874 A1 | 3/2018 | Au et al. |
| 2018/0117198 A1 | 5/2018 | Rovison, Jr. et al. |
| 2018/0271090 A1 | 9/2018 | Rovison et al. |
| 2018/0360060 A1 | 12/2018 | Pisanova et al. |
| 2019/0144313 A1 | 5/2019 | Block et al. |
| 2019/0152817 A1 | 5/2019 | Block et al. |
| 2019/0248679 A1 | 8/2019 | Rovison, Jr. et al. |
| 2019/0364892 A1 | 12/2019 | An et al. |
| 2019/0380337 A1 | 12/2019 | Mittiga et al. |
| 2019/0388574 A1 | 12/2019 | An et al. |
| 2020/0238887 A1 | 7/2020 | Rovison, Jr. et al. |

FOREIGN PATENT DOCUMENTS

| | | |
|---|---|---|
| EP | 0971584 | 1/2000 |
| WO | WO 2000/27964 | 5/2000 |
| WO | WO 2007/125101 | 11/2007 |
| WO | WO 2016/206729 | 12/2016 |

OTHER PUBLICATIONS

Written Opinion of the International Searching Authority for international application PCT/US2019/037957, filed Jun. 19, 2019; (corresponds to copending U.S. Appl. No. 17/253,953).

International Preliminary Report on Patentability for international application PCT/US2019/037957, filed Jun. 19, 2019; (corresponds to copending U.S. Appl. No. 17/253,953).

Asensio, et al., "Improvement of Biodegradable Biocide's Activity of Peroxyacetic Acid Bases Using Surfactants: Characterization and Stability," *Journal of Chemistry*, vol. 2015, Article ID 150206, 9 pages.

Certis: "Jet 5—Safety Data Sheet," pp. 1-8 (Aug. 9, 2007); XP55673415; http://www.interhort.com/_images/_attachments/1490.pdf.

Hanks, et al., "Evaluation of a Peroxyacetic Acid Disinfectant in Hot-water Treatment for the Control of Basal Rot (*Fusarium oxysporum* f. sp. narcissi) and Stem Nematode (*Ditylenchus dipsaci*) in Narcissus," *J. Phytopathology* 147:271-279 (1999).

U.S. Appl. No. 16/009,936, filed Jun. 15, 2018, US-2018-0360060 A1, Dec. 20, 2018, Pisanova.

U.S. Appl. No. 16/191,757, filed Nov. 15, 2018, US-2019-0144313 A1, May 16, 2019, Block.

U.S. Appl. No. 16/194,559, filed Nov. 19, 2018, US-2019-0152817 A1, May 23, 2019, Block.

U.S. Appl. No. 16/275,894, filed Feb. 14, 2019, US-2019-0248679 A1, Aug. 15, 2019, Rovison.

U.S. Appl. No. 16/428,216, filed May 31, 2019, US-2019-0364892 A1, Dec. 5, 2019, An.

U.S. Appl. No. 16/448,542, filed Jun. 21, 2019, US-2019-0388574 A1, Dec. 26, 2019, An.

U.S. Appl. No. 16/777,057, filed Jan. 30, 2020, US-2020-0238887 A1, Jul. 30, 2020, Rovison.

U.S. Appl. No. 17/253,953, filed Dec. 18, 2020, Mittiga.

\* cited by examiner

SOIL TREATMENT

CROSS-REFERENCE TO RELATED APPLICATIONS

This application claims priority under 35 U.S.C. § 119(e)(1) from U.S. Provisional Application Ser. No. 62/409,525, filed Oct. 18, 2016, the contents of which are incorporated herein by reference.

FIELD OF THE INVENTION

The present invention relates to compositions and methods for soil disinfection. The compositions and methods are useful against a variety of plant pathogens, including nematodes, bacteria, and fungi.

BACKGROUND OF THE INVENTION

Historically, methyl bromide ($CH_3Br$) had been the most widely used and most universal fumigant in the world. It is known for being extremely effective as a nematicide, insecticide, fungicide, and herbicide. Methyl bromide has been used extensively as a soil fumigant, a commodity quarantine treatment for exports and imports, as a pesticide on numerous crops, and as a structural fumigant applied to building surfaces. However, methyl bromide has contributed to the depletion of the ozone layer in the stratosphere. In accord with the Montreal Protocol, the import and manufacture of methyl bromide in the United States and other developed countries was banned in 2005. For developing countries, the reductions were more gradual and the phase-out was delayed until 2015.

Various compounds such as 1,3-dichloropropene, chloropicrin, metam sodium, and methyl iodide have been identified as alternatives to methyl bromide. While the alternative compounds do not cause depletion of stratospheric ozone, they all have limitations in activity or versatility as soil fumigants. They can be less effective than methyl bromide. They are commonly applied as mixtures of two or more of the individual compounds or in sequential applications in order to produce a broader spectrum product, resulting in reduced efficiency and increased costs for the user. Moreover, the toxicities associated with many alternative compounds present potential risks of worker exposure, contamination of crops and other plants with chemical residues, and environmental hazards such as ground water contamination.

Organic peracids, such as peracetic acid (PAA) are potent biocides. They have had limited utility as soil sterilants, in part, because the relatively high concentration of organic matter in soil may inactivate the peracids.

U.S. Pat. No. 5,168,655 discloses an aqueous solution comprising peracetic acid being made in-situ by mixing acetic acid, hydrogen peroxide, 2,6-pyridine dicarboxylic acid, dodecyl benzene sulphonic acid, and water. The solution is used in an irrigation system to partially control bacteria, fungal, spores, yeast, and molds in hydroponic substrates. U.S. Pat. No. 5,168,655 requires that the substrate contain only a minimal amount of organic matter because excessive amounts of organic matter, such as those in soil, are believed to inactivate the peracetic acid. Aromatic alkyl sulphonic acid, specifically odecyl benzene sulphonic acid, is disclosed as a wetting agent in the solution in U.S. Pat. No. 5,168,655.

EP 0035800 discloses an aqueous solution containing hydrogen peroxide and/or peracids having 1 to 4 carbon as soil treatment agent to control phytopathogenic harmful organisms, such as fungi, bacteria, and nematodes.

SUMMARY OF THE INVENTION

The present invention relates to an aqueous composition comprising a peracid and a polyoxyethylene alkylether carboxylic acid or a salt thereof. The peracid can be peracetic acid. The peracetic acid can be an aqueous equilibrium solution comprising a weight ratio of peracetic acid: hydrogen peroxide between 1:0.01 to 1:14 and a weight ratio of peracetic acid:acetic acid between 1:0.2 to 1:19. The peracetic acid concentration can be from about 3000 ppm to about 25,000 ppm. The polyoxyethylene alkylether carboxylic acid concentration can be from about 250 ppm to about 25,000 ppm. Also provided is a method of reducing the level of a pathogenic microorganism in an agricultural medium by contacting the agricultural medium with a composition comprising a peracid and a polyoxyethylene alkylether carboxylic acid or a salt thereof. The peracid can be peracetic acid. The pathogenic microorganism can be a nematode, bacteria, or fungus. The agricultural medium can include soil, sand, or a synthetic growth medium. The agricultural medium can be contacted with the composition by spraying, drenching, injecting, sprinkling, or infusing the composition into the agricultural medium. In some embodiments, the aqueous solution is applied at about 1.5 $mL/cm^2$ of agricultural medium.

DETAILED DESCRIPTION OF THE PREFERRED EMBODIMENT

This description of preferred embodiments is intended to be read in connection with the accompanying drawings, which are to be considered part of the entire written description of this invention. The drawing FIGURES are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing FIGURE under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

The present invention is directed to formulations for treatment of soil to control plant parasitic nematodes and soil-borne plant pathogens, for example, bacteria and fungi. The formulations include (i) peracids, such as peracetic acid and (ii) anionic surfactants, such as capryleth-9 carboxylic acid.

Peracetic acid is typically employed in the form of an aqueous equilibrium mixture of acetic acid (AA), hydrogen peroxide ($H_2O_2$) and peracetic acid (PAA). The weight ratios of these components may vary greatly, depending upon the particular grade of PAA employed. Among the grades of PAA which may be employed are those having a weight ratio of PAA:hydrogen peroxide between 1:0.01 to 1:14 and a weight ratio of PAA:acetic acid between 1:0.2 to 1:19. Commercially available peracetic acid solutions include 5% PAA with 22% $H_2O_2$ and 10.5% AA, 15% PAA with 10% $H_2O_2$ and 35% AA, 15% PAA with 23% $H_2O_2$ and 16% AA, 22% PAA with 10% $H_2O_2$ and 35% AA, and 35% PAA with 6.5% $H_2O_2$ and 40% AA.

The anionic surfactant can be a polyoxyethylene alkylether carboxylic acid, or a related anionic surfactant, including, for example, polyoxyethylene octyl ether carboxylic acid, polyoxyethylene(8) octyl ether carboxylic acid, polyoxyethylene(10) oleyl ether carboxylic acid, polyoxyethylene(10) lauryl ether carboxylic acid, polyoxyethylene(3) lauryl ether carboxylic acid, polyoxyethylene(5) lauryl ether carboxylic acid, polyoxyethylene(7) lauryl ether carboxylic acid, polyoxyethylene(2) oleyl ether carboxylic acid, polyoxyethylene(5) oleyl ether carboxylic acid, polyoxyethylene (9) oleyl ether carboxylic acid, and salts of above said polyoxyethylene alkylether carboxylic acids in sodium, potassium, or other cation forms. In some embodiments, the anionic surfactant is polyoxyethylene alkylether carboxylic acid, which is also known as Capryleth-9 Carboxylic Acid (denoted as C9CA).

Thus, the compositions of the invention can include a peracid, for example peracetic acid, and an anionic surfactant, for example, capryleth-9-carboxylic acid (C9CA). The peracid and the anionic surfactant can be diluted with water to the desired concentrations and combined at the point of use. Alternatively, or in addition, the peracid and the anionic surfactants can be combined to form a mixture and the mixture can be diluted with water before use. The peracid and the anionic surfactant can be combined and stored before use or they can be combined and used directly.

The compositions employed in the formulation of the invention can further include or exclude sequestrants such as dipicolinic acid and 1-hydroxyethylidene-1,1,-diphosphonic acid, as well as other ingredients such as mineral acid catalysts (sulfuric, nitric, or phosphoric acids); and short chain fatty esters (C6-C12) forming mixed peracids in solution.

In addition, the compositions employed in the formulation of the invention may further include or exclude one or more additional oxidants selected from the group consisting of chloroperbenzoic acid, perheptanoic acid, peroctanoic acid, perdecanoic acid, performic acid, percitric acid, perglycolic acid, perlactic acid and perbenzoic acid.

The compositions are diluted into water before use, and the diluted formulation can be applied using application techniques and equipment for soil fumigants in liquid form, such as trench applications, handgun applications, shank (chisel) applications, sweep or blade applications, drench application, and chemigation.

The present formulations may be used to control plant parasitic nematodes and soil-borne plant pathogens of bacteria and fungi. Exemplary plant parasitic nematodes include root knot nematodes such as *Meloidogyne hapla, Meloidogyne incognita, Meloidogyne enterolobii* and *Meloidogyne mayaguensis*; cyst nematodes such as soybean cyst nematodes (*Heterodera glycines*); potato cyst nematodes (*Globodera pallida* and *G. rostochiensis*) and cereal cyst nematodes (*Heterodera avenae* and *H. filipjevi*); root lesion nematodes such as (*Pratylenchus* spp., including *P. penetrans, P. thornei, P. neglectus, P. zeae, P. vulnus* and *P. coffeae*; and the burrowing nematode, *Radopholus similis*.

Exemplary soil bacteria include *Bacillus* species, for example *Bacillus mycoides*. Exemplary soil fungi include *Aspergillus* species, for example *Aspergillus niger*.

The following Examples are presented to offer further illustration of the present invention, but are not intended to limit the scope of the invention in any manner whatsoever.

EXAMPLES

Example 1

Peracetic acid formulations were evaluated for nematocidal and bactericidal activity. Formaldehyde was used as a positive control. The test conditions are described below and the results are summarized in Tables 1, 2, and 3.

Test method: A peracetic acid stock solution containing 5% PAA and 22% $H_2O_2$ (VigorOx® from PeroxyChem, LLC) was used for methods that specified 1750 ppm PAA. A peracetic acid stock solution containing 15% PAA and 10% $H_2O_2$ (VigorOx SP-15) was used for methods that specified 3525 ppm PAA. A stock solution of formaldehyde (37% in 10-15% methanol) was used to prepare a 1% aqueous solution of formaldehyde (with about 0.3% methanol).

Solutions were applied as the soil drench with an application volume of 12 kL/ha. The Test Medium was: pasteurized 50:50 Loamy sand or pasteurized sand. The efficacy of PAA was evaluated in three different Greenhouse Test Assays: 1) the Tomato Root-knot Galling Index Assay using the nematode species *Meloidogyne incognita* and *Meloidogyne hapla;* 2) the Root-knot Nematode Egg Hatch Assay using the nematode species *Meloidogyne incognita* and *Meloidogyne hapla*; and 3) assay of levels of soil bacteria using *Bacillus mycoides*.

The Root-knot Nematode Egg Hatch Assay was carried out essentially as follows. Eggs were collected from roots of infected tomato plants. To release the eggs, the egg masses were placed in a solution of sodium hypochlorite and manually shaken. The solution was centrifuged and the eggs washed with distilled water. Eggs were kept in the dark until needed for the experiments and used in the same day of collection. The experiments were performed in pots filled with pasteurized soil inoculated with about several thousands of individual eggs and then drenched with each treatment solution and controls. The treated soils were covered and incubated for the time periods indicated below. Following the incubation period, the soils were transferred to collect hatched J2 (second stage juveniles). The collected material was observed under the microscope and the number of J2 counted.

The results of the Root Knot Galling Index Assay are shown in Table 1. Seedlings were inoculated and cultivated for 28 days. Seedlings were then treated with either formaldehyde or 1750 ppm PAA for 27 days. Seedlings were harvested and the number of galls was determined. The Galling Index was on a scale of 0 to 10, where 0=no galling and 10=severe galling. A Galling Index of 3 or less is considered as commercial level control. As shown in Table 1, PAA alone at a dosage of 1750 ppm PAA applied as a soil drench to cells in the greenhouse provided only a modest reduction in the Galling Index that did not approach a commercial level of control.

TABLE 1

Effect of PAA on Tomato Root-knot Nematode Galling Index

| Treatment | Inoculation control | Formaldehyde at 1% | VigorOx at 1750 ppm PAA |
|---|---|---|---|
| Root-knot Galling Index | 8.5 | 2 | 7 |

The results of the Root Knot Nematode Egg Hatch Assay are shown in Table 2. Seedlings were inoculated and cultured in pasteurized Pemberton soil for 14 days. Seedlings were then treated with either formaldehyde, 1750 ppm PAA or 3525 ppm PAA for 13 days. Nematode eggs were extracted from infected roots and their ability to hatch was evaluated. As shown in Table 2, treatment of soil with 3525 ppm PAA resulted in a 51% reduction of the J2 (second stage juvenile) population relativity to control. Treatment of soil with 1750 ppm PAA did not reduce the J2 population relative to untreated controls. Treatment with 1% formaldehyde resulted in a 78% reduction relative to untreated controls.

TABLE 2

Effect of PAA Formulations on Root-knot Nematode Egg Hatch

| Treatment | Formaldehyde at 1% | VigorOx at 1750 ppm PAA | VigorOx SP-15 at 3525 ppm PAA[1] |
|---|---|---|---|
| % Reduction of J2 population | 78 | 0 | 51 |

The formulations were also assayed for the ability to reduce soil bacteria as shown in Table 3. Soil was inoculated with *Bacillus mycoides*, incubated for five days and then treated with formaldehyde or 1750 PPA for four days. Bacteria were collected from soil and their levels were evaluated based on colony forming units. As shown in Table 3, treatment of soil with 1750 ppm PAA resulted in a 47.5% reaction of colony forming units (CFU's) relative to control. Treatment of soil with 1% formaldehyde resulted in a 42.5% reduction of colony forming units (CFU's) relative to control.

TABLE 3

Effect of PAA on Bacteria in Soil

| Treatment | Formaldehyde at 1% | VigorOx at 1750 ppm PAA |
|---|---|---|
| % Reduction in population (CFU's) | 42.5 | 47.5 |

Example 2

Peracetic acid formulations were evaluated for nematocidal activity either alone or in combination with C9CA. Formaldehyde was used as a positive control.

Test method: A peracetic acid stock solution containing 15% PAA and 10% $H_2O_2$ (VigorOx SP-15) was used for methods that specified 3750, 5000, 7500, 10000 ppm PAA. Capryleth-9 carboxylic acid (C9CA) was used at concentrations of 5000 and 10000 ppm. A stock solution of formaldehyde (37% in 10-15% methanol) was used to prepare a 1% aqueous solution of formaldehyde. The final methanol concentration was about 0.3%.

Solutions were applied as a soil drench with an application volume of 12 kL/ha. The Test Medium was pasteurized Pemberton loamy soil, sand or pasteurized sand. The efficacy of PAA was evaluated with the Root-Knot Nematode Egg Hatch Assay using the nematode species *Meloidogyne incognita* and *Meloidogyne hapla*.

The results of the Root Knot Nematode Egg Hatch Assay are shown in Table 4. Seedlings were inoculated and cultured for 22 days and then treated for 21 days with either PAA alone at various concentrations, C9CA alone at various concentrations, or a combination of PAA and C9CA. Nematode eggs were extracted from infected roots and their ability to hatch was evaluated.

TABLE 4

Effect of PAA and C9CA on Root-knot Nematode Egg Hatch

| Treatment | | % Reduction of J2 Population |
|---|---|---|
| Formaldehyde At 1% | | 60 |
| Vigorox SP-15 | 3500 ppm PAA | 38 |
| | 5000 ppm PAA | 20 |
| | 7500 ppm PAA | 50 |
| | 10000 ppm PAA | 28 |
| C9CA | 5000 ppm | 0 |
| | 10000 ppm | 10 |
| Vigorox SP-15 + C9CA | 5000 ppm PAA + 5000 ppm C9CA | 40 |
| | 10000 ppm PAA + 10000 ppm C9CA | 60 |

Note:
22 days after inoculation; 21 days after treatment.

As shown in Example 2, PAA alone at a dosage between 3500 to 10000 ppm provided a moderate reduction in J2 nematode population in soil, which is consistent with the result in Example 1. C9CA provided minimal nematicidal activity when used alone at either 5000 ppm or 10000 ppm. When PAA and C9CA were used together, the effect on reduction of nematode population was substantially greater than the effect of either agent alone. PAA alone at 5000 ppm produced a 20% reduction in egg hatch. C9CA alone did not reduce the nematode population. But, the combination of PAA at 5000 ppm and C9CA at 5000 ppm resulted in a 40% reduction in the nematode population, as measured by Egg Hatch levels. This effect was also noted at higher concentrations of the agents. PAA alone at 10,000 ppm produced a 28% reduction nematode population. C9CA alone at 10,000 ppm produced a 10% reduction in nematode population. But, the combination of PAA at 10,000 ppm and C9CA at 10,000 ppm resulted in a 60% reduction in the nematode population, a reduction that was similar to that observed with the more toxic formaldehyde treatment. This synergistic effect was unexpected.

Example 3

Peracetic acid formulations were evaluated for nematocidal activity either alone or in combination with C9CA. Distilled water was used as a control in order to calculate the percentage of egg hatch that occurred in untreated soil.

Test method: A peracetic acid stock solution containing 15% PAA and 10% $H_2O_2$ (VigorOx SP-15) was used for methods that specified 3500 and 20,000 ppm PAA. Capryleth-9 carboxylic acid (C9CA) was used at concentrations of 250 and 10000 ppm.

Solutions were applied as a soil drench with an application volume of 1 ml/cm$^2$. The Test Medium was pasteurized sand-loam soil. The efficacy of PAA was evaluated with the Root-knot Nematode Egg Hatch Assay using the nematode species *Meloidogyne incognita* and *Meloidogyne hapla*.

The viability of the root-knot nematodes eggs used for each set of experiments in this example was also evaluated. Eggs were incubated with the different solutions in glass dishes in the dark at 25° C. They were observed daily under the microscope to confirm that the eggs were viable and able to hatch in water after 18 hr/24 hr of incubation. These observations confirmed that the eggs used for each set of soil experiments were viable.

The results of the Root Knot Nematode Egg Hatch Assay are shown in Table 5. Seedlings were inoculated and cultured for 22 days and then treated for 21 days with either PAA alone at various concentrations, C9CA alone at various concentrations, or a combination of PAA and C9CA. Nematode eggs were extracted from infected roots and their ability to hatch was evaluated.

TABLE 5

Effect of PAA and C9CA on Root-knot Nematode Egg Hatch

| Treatment | | % Egg Hatching |
|---|---|---|
| Distilled water | | 100 |
| VigorOx SP-15 | 20000 ppm PAA | 53 |
| C9CA | 250 ppm | 66 |
| VigorOx SP-15 + C9CA | 3500 ppm PAA + 250 ppm C9CA | 45 |
| | 200000 ppm PAA + 10000 ppm C9CA | 11 |

As shown in Table 5, soil treatment with PAA alone at 20,000 ppm had an inhibitory effect on egg hatching. Soil treatment with PAA alone at 20,000 ppm reduced egg hatching to 53% of distilled water treated control levels. Soil treatment with C9CA alone also had a modest inhibitory effect on egg hatching. Soil treatment with C9CA alone at 250 ppm reduced egg hatching to 66% of distilled water treated control levels. Consistent with the results shown in Example 2, when PAA and C9CA were used together, the effect on reduction of nematode population was substantially greater than the effect of either agent alone. Moreover, the inhibitory effect was dose-dependent. Soil treatment with 3500 ppm PAA+250 ppm C9CA reduced egg hatching to 45% of distilled water treated control levels. Soil treatment at higher doses, (20000 ppm PAA+10000 ppm C9CA) reduced the percentage of egg hatching to only 11% of distilled water treated controls. This synergistic effect was unexpected.

Example 4

Peracetic acid formulations were evaluated for sporicidal activity.

Test method: A peracetic acid stock solution containing 15% PAA and 10% $H_2O_2$ (VigorOx SP-15) was used for methods that specified 3525 ppm PAA. Deionized water was used as a control.

Solutions were applied as the soil drench with an application volume of 1.5 ml/cm$^2$. The Test Medium was pasteurized Pemberton soil. The spore inoculum was *Bacillus subtilis* ATCC 19659. Spores were counted as follows: Soil was pasteurized to remove background microbial content. The soil was distributed into test cells. Concentrated *Bacillus subtilis* ATCC 19659 spore suspension was diluted in Butterfield's buffer and used as the inoculum in this test. For titer determination, the inoculum was diluted in Butterfield's buffer and plated on Petrifilm APC. In order to test for antimicrobial efficacy following treatments, soil was scooped from the cell and measured into a sterile plastic centrifuge tube. Deionized water was then added to each soil sample. The tubes were then capped, shaken to suspend soil, and vortexed at maximum speed using the lab vortex. The samples were allowed to settle for several seconds, and then 2 mL of fluid was removed from the tube. One ml of the removed sample was diluted in 9 mL Butterfield's buffer. The remainder of the removed sample was plated onto Petrifilm APC. The diluted sample was further serially diluted and plated on APC. The plates were all incubated at 30±2° C. for 2-5 days and then colonies on the plates were counted.

The results of the sporicidal assay are shown in Table 6. As shown in Table 6, no bacterial spores capable of giving rise to viable colonies were recovered after both short (1 hour) and longer (2 and 7 days) treatment with PAA level of 3525 ppm.

TABLE 6

Sporicidal effect of PAA

| Treatment | Time | $Log_{10}$ CFU | $Log_{10}$ Reduction |
|---|---|---|---|
| VigorOx SP-15 | 1 hour | 0 | Total kill |
| | 2 days | 0 | Total kill |
| | 7 days | 0 | Total kill |
| DI Water Control | 1 hour | 2.1 | N/A |
| | 2 days | 2.3 | N/A |
| | 7 days | 2.2 | N/A |

Example 5

PAA was evaluated either alone or in combination with C9CA for fungicidal activity.

Test method: A peracetic acid stock solution containing 15% PAA and 10% $H_2O_2$ (VigorOx SP-15) was used for methods that specified 3500 and 20,000 ppm PAA. Capryleth-9 carboxylic acid (C9CA) was used at concentrations of 5000 and 30,000 ppm.

Solutions were applied as a soil drench with an application volume of 1.5 ml/cm$^2$. The Test Medium was pasteurized Pemberton soil. The spore inoculum was *Aspergillus niger* ATCC 16404. The fungicidal activity of the compositions was evaluated as follows: Soil was pasteurized to remove background microbial content. The soil was the filled into test cells. *Aspergillus niger* ATCC 16404 was grown on Potato Dextrose Agar (PDA) plates for 5 days at 35° C. A culture for test was prepared by washing a plate with Butterfield's buffer, grinding in a sterile tissue grinder, and filtering through a cell filter to remove hyphae and debris. The suspension was diluted 1:100 in Butterfield's buffer and was added to the soil as the inoculum. The inoculum was enumerated on Petrifilm APC to determine the titer. In order to analyze antimicrobial efficacy following the treatments, soil was scooped from the cell and weighed into a sterile plastic cup. Sterile deionized water was added to the cup using a serological pipette. The cups were then capped, shaken to suspend soil, and vortexed at maximum speed using the lab vortex. The samples were allowed to settle for several seconds, and then 2 mL of fluid was removed from the tube. One ml of the removed fluid was diluted in 9 mL Butterfield's buffer. The remaining removed fluid was plated onto Petrifilm Petrifilm YM. The diluted sample was further serially diluted and plated to $10^{-3}$ on YM. The plates were all incubated at 35±2° C. for 3 to 4 days and colonies were counted.

TABLE 7

Fungicidal effect of PAA and C9CA

| Treatment | Time | $Log_{10}$ CFU | $Log_{10}$ Reduction |
|---|---|---|---|
| 3500 ppm PAA | 1 hour | 3.2 | 2.4 |
|  | 24 hours | 0.0 | Total kill |
| 7500 ppm PAA | 1 hour | 0.0 | Total kill |
|  | 24 hours | 0.0 | Total kill |
| 3500 ppm PAA + | 1 hour | 3.6 | 2.0 |
| 5000 ppm C9CA | 24 hours | 0.0 | Total kill |
| 7500 ppm PAA + | 1 hour | 0.0 | Total kill |
| 5000 ppm C9CA | 24 hours | 0.0 | Total kill |
| 3500 ppm PAA + | 1 hour | 3.4 | 2.2 |
| 30000 ppm C9CA | 24 hours | 0.0 | Total kill |
| Untreated | 1 hour | 5.6 | N/A |
| control | 24 hours | 5.5 | N/A |

As shown in Table 7, PAA alone provided a $Log_{10}$ reduction of more than 2 at even at the short treatment time of one hour. *Aspergillus niger* was completely eliminated after 24 hrs of treatment. Doubling the PAA dosage to 7000 ppm resulted in complete elimination even after only one hour of treatment.

From the foregoing, it will be appreciated by those skilled in the art that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method of reducing the concentration of nematodes as a pathogenic microorganism in an agricultural medium comprising soil or sand, the method comprising applying an aqueous composition comprising a peracid and a polyoxyethylene alkylether carboxylic acid or a salt thereof to the agriculture medium at a concentration and for a time sufficient to reduce the concentration of the nematodes.

2. The method of claim 1, wherein the nematodes are selected from the group consisting of: root knot nematodes; cyst nematodes; root lesion nematodes; and burrowing nematodes.

3. The method of claim 1, wherein the peracid is peracetic acid.

4. The method of claim 3, wherein the peracetic acid is an aqueous equilibrium solution comprising a weight ratio of peracetic acid:hydrogen peroxide of between 1:0.01 to 1:14 and a weight ratio of peracetic acid:acetic acid 1:0.2 to 1:19.

5. The method of claim 3, wherein the peracetic acid concentration is from 3000 ppm to 25,000 ppm.

6. The method of claim 1, wherein the polyoxyethylene alkylether carboxylic acid concentration is from 250 to 25,000 ppm.

7. The method of claim 1, wherein the aqueous composition is applied by spraying, drenching, injecting, sprinkling or infusing the aqueous composition into the agricultural medium.

8. The method of claim 1, wherein the aqueous composition is applied at 1.5 mL/cm$^2$ of the agricultural medium.

9. The method of claim 1, wherein the nematode is a root knot nematode selected from the group consisting of: *Meloidogyne hapla*; *Meloidogyne incognita*; *Meloidogyne enterolobii*; and *Meloidogyne mayaguensis*.

10. The method of claim 4, wherein the peracetic acid concentration is from 3000 ppm to 25,000 ppm.

11. The method of claim 10, wherein the nematodes are selected from the group consisting of: root knot nematodes; cyst nematodes; root lesion nematodes; and burrowing nematodes.

12. The method of claim 3, wherein the polyoxyethylene alkylether carboxylic acid concentration is from 250 to 25,000 ppm.

13. The method of claim 12, wherein the aqueous composition is applied by spraying, drenching, injecting, sprinkling or infusing the aqueous composition into the agricultural medium.

14. The method of claim 13, wherein the aqueous composition is applied at 1.5 mL/cm$^2$ of the agricultural medium.

15. The method of claim 14, wherein the nematode is a root knot nematode selected from the group consisting of: *Meloidogyne hapla*; *Meloidogyne incognita*; *Meloidogyne enterolobii*; and *Meloidogyne mayaguensis*.

16. The method of claim 2, wherein the polyoxyethylene alkylether carboxylic acid concentration is from 250 to 25,000 ppm.

17. The method of claim 16, wherein the aqueous composition is applied by spraying, drenching, injecting, sprinkling or infusing the aqueous composition into the agricultural medium.

18. The method of claim 17, wherein the aqueous composition is applied at 1.5 mL/cm$^2$ of the agricultural medium.

19. The method of claim 1, wherein the method reduces the concentration of nematodes by at least 40%.

* * * * *